(12) United States Patent
Modi

(10) Patent No.: US 9,241,921 B2
(45) Date of Patent: Jan. 26, 2016

(54) PHOTOSENSITIZER COMPOSITION FOR TREATING SKIN DISORDERS

(76) Inventor: Pankaj Modi, Ancaster (CA)

( * ) Notice: Subject to any disclaimer, the term of this patent is extended or adjusted under 35 U.S.C. 154(b) by 424 days.

(21) Appl. No.: 13/098,844

(22) Filed: May 2, 2011

(65) Prior Publication Data

US 2012/0283328 A1 Nov. 8, 2012

(51) Int. Cl.
*A01N 37/02* (2006.01)
*A01N 37/06* (2006.01)
*A61K 31/225* (2006.01)
*A01N 37/00* (2006.01)
*A61K 31/19* (2006.01)
*A61K 31/197* (2006.01)
*A61K 45/06* (2006.01)
*G01N 33/574* (2006.01)

(52) U.S. Cl.
CPC .............. *A61K 31/197* (2013.01); *A61K 45/06* (2013.01); *G01N 33/5743* (2013.01)

(58) Field of Classification Search
USPC ........................................................ 514/547
See application file for complete search history.

(56) References Cited

U.S. PATENT DOCUMENTS

| | | | |
|---|---|---|---|
| 4,956,171 A | 9/1990 | Chang | |
| 5,156,846 A | 10/1992 | Petersen et al. | |
| 5,326,566 A | 7/1994 | Parab | |
| 6,559,183 B1 | 5/2003 | Schmid et al. | |
| 7,659,301 B2 * | 2/2010 | Anderson et al. | 514/410 |
| 2002/0054918 A1 * | 5/2002 | Murad | 424/616 |
| 2008/0069857 A1 * | 3/2008 | Yeo et al. | 424/426 |

FOREIGN PATENT DOCUMENTS

| | | |
|---|---|---|
| DE | 4435805 | 4/1996 |
| KR | 963162 B1 * | 6/2010 |

OTHER PUBLICATIONS

Wolf, et al., Topical photodynamic therapy with endogenous porphyrins after application of 5-aminolevulinic acid. Journal of the American Academy of Dermatology, vol. 28, Issue 1, Jan. 1993, pp. 17-21.
Vonarx, V. et al. "Potential Efficacy of the Delta 5-Aminolevulinic Acid Bioadhesive Gel Formulation for the Photodynamic Treatment of Lesions of the Gastrointestinal Tract in Mice", J. Pharm. Pharmacol. 1997, 49: pp. 652-656.
Peng, et al. "5-Aminolevulinic acid-based photodynamic therapy: Clinical research and future challenges", Cancer, 1997, 79(12), pp. 2282-2308.

* cited by examiner

*Primary Examiner* — Layla Soroush

(57) ABSTRACT

A composition comprising an active ingredient selected from the group of 5-aminolevulinic acid or a pharmaceutically acceptable salt or derivative thereof; and an aqueous carrier comprising at least one absorption enhancer, an anesthetic, hyaluronic acid and at least one acid selected from the group consisting of glycolic acid and lactic acid. The composition is useful in a photodynamic method of treating skin disorders.

16 Claims, 4 Drawing Sheets

A.

B

A)

B)

A)

B)

C)

PHOTOSENSITIZER COMPOSITION FOR TREATING SKIN DISORDERS

FIELD OF THE INVENTION

The present invention relates to a composition for treating skin disorders, and more particularly, to a composition comprising a photosensitizer.

INTRODUCTION

The growing incidence of cutaneous malignancies each year necessitates the development of new and more effective methods for both the diagnosis and the treatment of cancerous lesions, while assuring better cosmetic results and improving patient satisfaction. With that in mind, the use of topical photodynamic therapy (PDT) has been explored for use as a treatment as well as for use in the diagnosis of various cutaneous malignancies. Using the intrinsic cellular haem biosynthetic pathway and principles of photo-illumination, topical PDT carries the goal of selectively targeting abnormal cells, while preserving the normal surrounding structures.

Photosensitization can be achieved either by administration of exogenous photosensitizing molecules (porphyrins, chorins, phthalocynines) or by taking advantage of endogenous pathways through the application of precursors, such as 5-aminolaevulinic acid (5 ALA) or its derivatives. The preferential accumulation of photodynamically active porphyrins in tumour lesions in comparison with healthy tissue may be due to various mechanisms such as differences in cellular uptake mechanisms (i.e. variously expressed transmembrane transporters), activities of the haem synthesis enzymes, iron availability, properties of the stratum corneum and variable tissue penetration and distribution.

Many photosensitizers are lipophilic and accumulate in membrane structures, damaging both the plasma membrane as well as mitochondrial structures. Furthermore, cellular microtubules and spindle apparatus essential for mitotic division are sensitive to PDT. The net result is cell death by necrosis and apoptosis. It is important to note that although PDT results in singlet oxygen species, these reactive radicals are short lived, with a radius of action of only 0.01 µm, and therefore have very low mutagenic potential for DNA damage. On the tissue level, PDT has been found to act on both the tumour as well as on the tumour's vascular supply. It is postulated that water-soluble sensitizers have a greater affinity for the vascular system, while lipophilic molecules have a direct effect on the tumour itself.

5-ALA is an amino acid and is among the first molecules noted to be effective in photosensitization of cells. However, 5-ALA itself is not a photosensitizer. Topically applied, 5-ALA and its ester derivatives take advantage of the intrinsic cellular heme biosynthetic pathway to produce photoactive porphyrins. Using a series of enzymatic reactions between the mitochondria and the cytosol, 5-ALA is ultimately converted to protoporphyrin IX as shown if FIG. 1A. This fluorescent molecule, through its extensive network of alternating double bonds, is essential to the transference of singlet oxygen species and the formation of free radicals. The rate of porphyrin synthesis through this pathway is significantly higher in malignant or pre-malignant cells, approximately between two- and 10-fold, with a 10:1 ratio of porphyrin induction in skin tumours to surrounding tissue. FIG. 1B illustrates the fluorescense excitation spectrum of protoporphyrin IX, demonstrating the essential role of the 407-420 nm blue-band in photo-destruction.

Topical compositions of 5-aminolevulinic acid are known. For example, Thiele et al. (H+G, Volume 69, No. 3, pages 161-164 (1994)) describe a δ-aminolevulinic acid composition in the form of an oil-in-water emulsion having a penetration period of from 5 to 6 h. Subsequent irradiation with an argon ion-pumped dye laser (emission maximum 630 nm) yielded a cumulative total dose of from 50 to 100 $J/cm^2$. Wolf et al. (Journal of the American Academy of Dermatology Vol. 28, pages 17 to 21, 1993) also describe a 5-aminolevulinic acid composition in the form of an oil-in-water emulsion having a penetration period of 4, 6 or 8 h. Irradiation with unfiltered light or red light resulted in a dose of from 30 $J/cm^2$ to 100 $J/cm^2$.

However, the use of 5-aminolevulinic acid in an oil-in-water emulsion for photodynamic therapy has a number of disadvantages. Rodriguez et al. (SPIE, Vol. 2371, pages 204-209) showed that, in the high concentrations which are required for a clinical application, aminolevulinic acid is unstable in aqueous solutions in the neutral to basic pH range. In a 25 hour time period, satisfactory results are only obtained at a pH of 5.01. A concentration of 3% and a pH of 5 are specified as the optimal conditions for aqueous solutions of 5-aminolevulinic acid. However, for clinical use, generally 5-ALA compositions in a higher concentration range will be required. Furthermore, to be used commercially, the 5-ALA solutions must be stable for a sufficient period of time, e.g. in the order of weeks or months.

V. von Arx et al. (J. Pharm. Pharmacol. 49: 652-656, 1997) describe the topical application of 5-aminolevulinic acid in a variety of gels. This publication states that the best formulation for maintaining the stability of 5-aminolevulinic acid is a combination with Novion AA-1, a polyacrylic acid, at a pH<6.

Another disadvantage of the known 5-ALA oil-in-water emulsions relates to a depth of penetration of the photosensitizer which is not optimal. The use of penetration or permeation enhancers has been found to be critical to achieve a consistent supply of a therapeutically active ingredient at the site of action during the treatment of skin diseases. For example, as described in U.S. Pat. No. 5,326,566, a composition of such systemically effective pharmacological agents in combination with dibutyl adipate, or a mixture of dibutyl adipate and isopropyl myristate, can greatly enhance the rate of penetration of agents through the skin and can increase the amount absorbed into the systemic circulation. Although a variety of permeation enhancing agents have been used for enhancing the absorption of therapeutic agents into and through the skin, serious problems can arise when permeation enhancers are incompatible with a given drug over a long time period, thereby resulting in drug instability and degradation when the enhancers and the drug are co-formulated into a pharmaceutically acceptable composition for use in warm-blooded mammals, including humans.

Petersen et al., U.S. Pat. No. 5,156,846, discloses a percutaneous drug delivery system and method which requires pretreating the skin with a skin permeation enhancer, which is an enzyme preparation, and occluding the area of the skin to which the skin permeation enhancing enzyme preparation is applied, removing the skin occlusion means, and applying a drug after rinsing the area. It is disclosed that the skin can again be occluded following application of the drug on the enzyme-pretreated site.

Y. Chang, U.S. Pat. No. 4,956,171, teaches a transdermal drug delivery system having a dual permeation enhancer in which the specific permeation enhancers are sucrose cocoate and methyl laurate. These two enhancers are required for use due to their ability to synergize for penetration enhancement.

German Patent Application No. DE4435805-A1 discloses formation of an enzyme cream at the site of application from an enzyme-containing anhydrous ointment base and an aqueous tenside-containing oily emulsion (or a mixture of emulsifiers) which are packaged separately. The cream is disclosed to provide enzyme stability and maximum activity at the application site.

In view of the foregoing, it would be desirable to develop a composition comprising a photosensitizer that overcomes at least one of the disadvantages of known compositions.

SUMMARY OF THE INVENTION

An aqueous composition comprising 5-aminolevulinic acid, or a derivative thereof, in combination with a carrier comprising an absorption enhancer in the aqueous phase has been found to be advantageous over prior compositions for use in a photodynamic treatment of skin disorders.

Thus, in one aspect, a composition is provided comprising:
1) an active ingredient selected from the group of 5-aminolevulinic acid or a pharmaceutically acceptable salt or derivative thereof; and
2) an aqueous carrier comprising at least one absorption enhancer, an anesthetic, hyaluronic acid and at least one acid selected from the group consisting of glycolic acid and lactic acid.

In another aspect, a method of treating a skin disorder in a mammal is provided comprising topically administering a composition comprising an ALA active ingredient to a target site on the mammal and irradiating at least a portion of the target site with light at a wavelength that activates the active ingredient.

In a further aspect, a process for preparing an ALA composition is provided. The process comprises the steps of preparing an aqueous carrier comprising at least one absorption enhancer, at least one of lactic acid and glycolic acid, hyaluronic acid and an anaesthetic, and combining the aqueous carrier with an active ingredient selected from the group of 5-aminolevulinic acid or a pharmaceutically acceptable salts or derivatives thereof, until the active ingredient is dissolved.

These and other aspects of the invention are described by reference to the following figures.

DETAILED DESCRIPTION OF THE INVENTION

Figure 1:
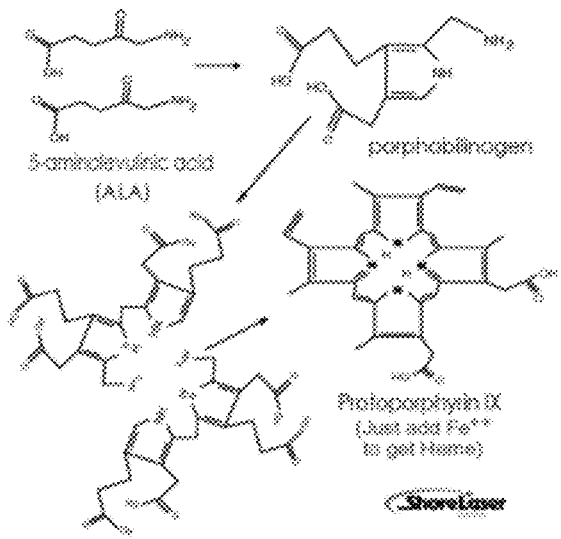
FIG. 1 illustrates the formation of photoporphyrin IX from 5-aminolevulinic acid when exposed to UV light (A) and the fluorescense excitation spectrum of protoporphyrin IX (B)
Figure 1:
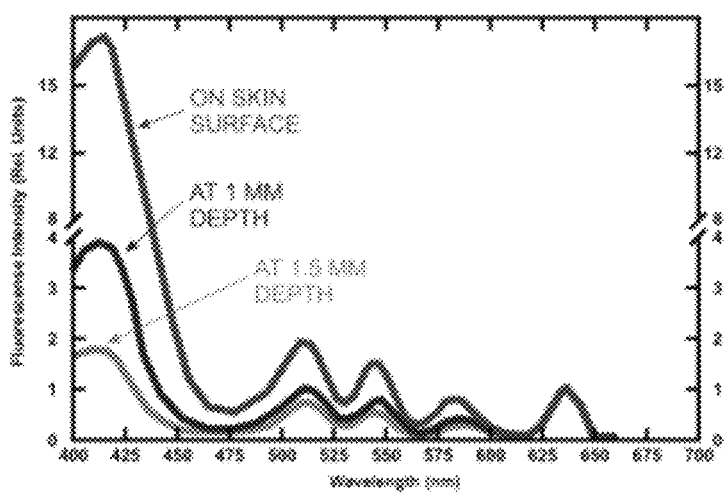

A composition useful to treat a skin disorder is provided comprising an active ingredient selected from the group of 5-aminolevulinic acid or a pharmaceutically acceptable salt or derivative thereof; and an aqueous carrier comprising at least one absorption enhancer, an anesthetic, hyaluronic acid and at least one acid selected from the group consisting of glycolic acid and lactic acid.

The composition comprises 5-aminolevulinic acid (5-ALA) or a pharmaceutically acceptable salt or derivative thereof which are capable of being converted in a cell into protoporphyrin IX. Suitable salts include acid addition salts and suitable derivatives of 5-ALA include methylaminolevulinate (MAL) and hexylaminolevulinate (HAL), as well as methyl, butyl, hexyl, and octyl-5-ALA ester derivatives. The term "ALA" is used herein to encompass 5-ALA, and pharmaceutically acceptable salts and derivatives thereof.

The aqueous carrier may be any carrier that is able to form micelles in an aqueous phase, e.g. preferably to form a nano-micellar solution. The carrier comprises an acidic phase, i.e. a material which is miscible with water and is a physiologically harmless carrier substance, which imparts on the composition a pH of less than 7, preferably less than 6, and more preferably, a pH of less than about 4 to 5. Suitable carrier systems, which are stable over a long period of time, may contain suitable concentrations of surfactants and cosurfactants, and are free from toxic emulsifier complexes. Such carriers may comprise a glycerophosphatide, such as a lecithin or a cephalin, as the emulsifier and physiologically tolerated lipids, e.g. triglycerides, such as vegetable or animal oils, for example groundnut oil, soybean oil, etc., as the oil phase. Examples of other suitable emulsifiers include egg lecithin, soybean lecithin and phosphatidyl choline. An example of an approved lipid is Miglyol 812. The emulsifier/oil weight ratio may be from about 0.05 to 0.4:1.

The aqueous carrier additionally includes one or more absorption enhancers. Suitable absorption enhancers include sodium lauryl sulfate, sodium dodecyl sulfate, DMSO, bile salts, compound selected from the group comprising lecithin, hyaluronic acid, octylphenoxypolyethoxyethanol, chamomile extract, cucumber extract, oleic acid, glycolic acid, lactic acid, water, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, cholates such as cheodeoxycholate, sodium glycolcholate and deoxycholate, lidocaine, benzyl alcohol, carbomer 940, cholesterol, hydrogenated lecithin, polysorbate 80, propylene glycol, trolamine, vitamin E acetate, lidocaine, benzyl alcohol, carbomer 940, cholesterol, hydrogenated lecithin, polysorbate 80, propylene glycol, trolamine, vitamin E acetate and combinations thereof.

The aqueous carrier also comprises an anaesthetic suitable for topical application. Examples of suitable anaesthetics include Lidocaine, bupivacaine, prilocaine, benzocaine, tetracaine, lanacaine, mepivacaine and combinations thereof.

The present composition may additionally comprise an oxygen radical generating compound, e.g. a peroxide such as hydrogen peroxide or benzoyl peroxide, or an oxygen-retaining compound such as a perfluorocarbon, e.g. an octafluoropropane, perfluorohexane and perfluorodecalin, that retains gaseous oxygen. An amount of either of these compounds in the range of about 1% to 20% by weight in the composition is useful to enhance the therapeutic effect of the composition by supplementing the oxygen radical content at the target site, thereby enhancing treatment.

The composition may additionally comprise cosmetic or pharmaceutical adjuvants such as buffers, pH modifiers, stabilizers, additional emulsifiers, thickeners, and the like. Examples of suitable such adjuvants include emulsifiers such as glycerophosphatide, such as a lecithin or a cephalin, physiologically tolerated lipids, e.g. triglycerides, such as vegetable or animal oils, for example groundnut oil, soybean oil, stabilizers such as HA, octylphenoxypolyethoxyethanol, glycolic acid and lactic acid, and thickeners and/or buffers such as oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, benzyl alcohol, carbomer 940, cholesterol, hydrogenated lecithin, polysorbate 80, propylene glycol, trolamine and vitamin E acetate.

The concentration of the ALA active ingredient in the composition is in the range of about 0.1 to about 30 percent by weight, preferably from about 0.1 to about 20 percent by weight, and most preferably from about 10 to about 20 percent by weight of the total composition. The composition additionally comprises a carrier in an amount of about 40-60% by weight comprising about 0.1-10% of an absorption enhancer, about 0.1-20% glycolic acid, lactic acid or both and about 0.1-10% anaesthetic, based on the total weight of the composition. In one embodiment, the absorption enhancer includes HA and PVA, in amounts, for example, of about 0.1-2% HA and about 0.1-2% PVA.

In one embodiment, the composition is in the form of a solution and comprises, based on the total weight of the composition, from 1 to 15% of active ingredient, from 5 to 55% of carrier and from 1 to 5% of adjuvants, with the remainder being water. In another embodiment, the composition is in the form of a lotion, and based on the total weight of the composition, comprises from 1 to 15% of active ingredient, from 1 to 25% of carrier and from 1 to 25% of adjuvants, with the remainder being water.

In a particularly preferred embodiment, the composition according to the invention is a solution which, based on the total weight of the composition, comprises from 1 to 25% by weight, preferably from 5 to 15% by weight, of active ingredient, from 40 to 60% by weight, preferably from 45 to 55% by weight, of carrier and from 0 to 10% by weight, preferably from 1 to 5% by weight, of adjuvants, with the remainder being water.

According to another particularly preferred embodiment, the composition according to the invention is a lotion which, based on the total weight of the composition, comprises from 1 to 25% by weight, preferably from 5 to 15% by weight, of active substance, from 10 to 30% by weight, preferably from 15 to 25% by weight, of carrier and from 10 to 30% by weight, preferably from 15 to 25% by weight, of adjuvants, with the remainder being water.

A process for preparing the present ALA composition is also provided. The process comprises the steps of preparing an aqueous carrier comprising at least one absorption enhancer, at least one of lactic acid and glycolic acid, hyaluronic acid and an anaesthetic. The components of the carrier may be mixed, for example, using a commercially available high pressure mixer or homogenizer. The aqueous carrier is then mixed with an active ALA ingredient selected from the group of 5-aminolevulinic acid or a pharmaceutically acceptable salt or derivatives thereof, until the active ingredient is dissolved. The active ALA compound may be combined with the carrier in the form of a powder or crystals, or may first be dissolved in a diluent. Preferably, the active ingredient is prepared into a solution by admixture with a diluent such as water or a water/alcohol mix, such as ethyl alcohol and water in amounts ranging from about 20%-90% alcohol and then combined with the carrier. The carrier may be in the form of a nano-micellar solution prior to the addition of the ALA compound, or may be converted to a nano-micellar solution subsequent to the addition of ALA. Adjuvants and any other desired additives may be added to the composition following the addition of ALA.

Preference is given to excluding air while carrying out the process, for example by means of applying a vacuum and/or a protective gas atmosphere. In addition, it is preferred to implement the process while excluding light. The process is carried out at a temperature at which the desired micellar solution can be formed and the constituents, in particular the active ingredient, is adequately stable. In general, it has been found that a temperature range of from about 5 to 45° C. is suitable. However, adjuvants and/or additives which are, for example, mixed and homogenized, where appropriate, in a separate mixture, can be processed at higher temperatures if needed, for example up to about 80° C., and then added to the composition. For a pharmaceutical application, care is taken to ensure that the resulting product is prepared and administered at a room temperature, preferably at 25° C., and prepared in a sterile environment for example by employing sterile starting materials and maintaining sterile process conditions and/or by inserting a sterilization step after the preparation.

The present ALA composition is useful to treat a skin disorder. The term "skin disorder" as used herein is meant to encompass skin abnormalities such as contact dermatitis, rash, housewives' eczema, atopic dermatitis, seborrheic dermatitis, lichen Vidal, prurigo, drug eruption, solar dermatitis, pruritus cutaneous, psoriasis, acne, acne vulgaris, erythema, as well as a cell proliferation disorder including cancer, such as carcinoma, malignant skin cancers such as basal cell carcinoma, squamous cell carcinoma, Bowen's disease, solar keratosis, condylomata acuminata (CIN), intraepithelial neoplasia of the vulva (VIN), a nodose cancer and a subcutaneous cancer.

Typically, the ALA composition of the invention is administered topically in the treatment of a skin disorder in the form of a solution, gel or lotion, depending on the components and the component amounts in the composition.

The present composition may also be prepared for systemic administration, such as an injectable liquid. However, for dermatological and gynecological applications, the composition is preferably in a form which is suitable for topical administration. The composition possesses properties, e.g. viscosity and rheology, that may be adjusted to achieve the administrable form which is in each case required in order to ensure that, after the composition has been administered, the active ingredient penetrates to an adequate extent into the target tissue. These viscosity and rheology properties can be adjusted by adding thickeners such as polyethylene glycol stearyl ethers, polyethylene glycol stearates and/or polysaccharides such as polysaccharide B-1459, sodium hyaluronic acid and hydroxypropyl methyl cellulose.

In another aspect of the invention, a method of treating a skin disorder in a mammal is provided. The method comprises topically administering an ALA composition to a target site in the mammal and irradiating at least a portion of the target site with light at a wavelength that activates the active ingredient. In one embodiment, the ALA composition is allowed to penetrate the target site, e.g. permeate the skin, for a suitable penetration period prior to irradiation of the target site. The penetration period may be from about 10 minutes to about 12 hours, preferably from about 10 minutes to about 60 minutes, and most preferably from about 10 to minutes to 15 minutes. As a general practice, the target site is covered following application of the ALA composition, with a material reduces evaporation of components in the carrier. An example of a suitable material is plastic.

Following application of the ALA composition, the target site is irradiated with light that activates the active ALA ingredient, for example, a wavelength of the light in the range of between about 320 and about 700 nm, and more preferably a wavelength in the range of about 400 to about 600 nm. Any suitable light source may be used to irradiate the target site including: laser diodes; light emitting diodes; electroluminescent light sources; incandescent light sources; cold cathode fluorescent light sources; organic polymer light sources; inorganic light sources; blue light; or UV visible lights. Other suitable light sources include lamps which emit white light and also monochromatic light sources, such as a laser, in particular an argon dye laser which emits at about 630 nm. The radiation doses are normally in a range of from about 20 J/cm$^2$ to several hundred J/cm$^2$ per application.

In one embodiment, the active ALA ingredient and the carrier (including the permeation enhancer) are individually topically applied to a target site on the skin of a mammal, and mixed directly on the skin to produce the desired active composition. This in situ mixing of active ingredient and permeation enhancer advantageously increases the level or extent of penetration of the active ingredient into the skin in comparison to a pre-mixed composition.

The stability of the present ALA composition is substantially increased in comparison to 5-ALA itself. This is due to the low pH (e.g. pH of about 1.5-3) of the carrier which comprises glycolic and/or lactic acid components. While the reasons for this are not known, it appears that a microenvironment created by the enhancers as micelles has a particularly favorable effect on the stability of the 5-aminolevulinic acid. In this regard, the stability of the composition is evidenced by the stability of the ALA active ingredient. After one year of storage at room temperature, the amount of active ingredient has not decreased by more than 5% and, preferably, by not more than 4%. After one year of storage at 5° C., the amount of active ingredient is preferably reduced by not more than 3% and preferably by not more than 2.5%.

In addition, very high tissue penetration depths are achieved with the present ALA composition which permits the treatment of deep-lying diseases, such as actnic keratosis, acne vulgaris, contact dermatitis, rash, housewives' eczema, atopic dermatitis, seborrheic dermatitis, lichen Vidal, prurigo, drug eruption, solar dermatitis, pruritus cutaneous, psoriasis, or erythema, carcinoma, non-malignant melanoma, or diseases in which penetration of very thick layers of tissue is required. Determination of penetration depth was determined using a standard fluorescence measurement technique on tissues samples (obtained by the punch biopsy) suspended in the water and measuring the fluorescence emissions at 460 nm.

The active ingredient of the present composition is advantageously taken up very efficiently by the cells. This improves targeting, and reduces the penetration period, i.e. the time between applying the composition and irradiating the diseased tissue with light, both desirable for improved treatment. Thus, incubation time once the present ALA composition is applied to a target site is about 10-20 minutes before irradiation. This is compared to currently available ALA compositions which require an incubation time of at least 1 to 4 hrs or sometimes even longer which is highly impractical for both doctor and patient.

In a further aspect, the present ALA compositions may be used to detect the presence of proliferating cells in a sample, for example a tissue sample. The detection is based on selectively concentrating a photosensitizer, which is produced by metabolism of the active substance, in proliferating cells as compared with normal cells. Preference is given to the active substance being 5-aminolevulinic acid and the photosensitizer being protoporphyrin IX. The extent to which the photosensitizer has been concentrated can be determined by means of photodiagnostic methods, for example by irradiating with light having a wavelength of 405-420 nm and measuring the fluorescence radiation generated by the photosensitizer. Topically applied, 5-ALA and its ester derivatives take advantage of the intrinsic cellular heme biosynthetic pathway to produce photoactive porphyrins. Using a series of enzymatic reactions between the mitochondria and the cytosol, 5-ALA is ultimately converted to protoporphyrin IX. This fluorescent molecule, through its extensive network of alternating double bonds is essential to the transference of singlet oxygen species and form this singlet oxygen in enough concentration.

Finally, a kit is provided which comprises an ALA composition, which may be an emulsion, according to the invention, which is suitable for being applied topically, and one or more auxiliary substances. Examples of these auxiliary substances are a covering material, such as a plastic film which is applied to the site being treated, after the emulsion has been applied, in order to prevent premature activation by light, and means for attaching the covering material or means for applying the emulsion to the site being treated.

Embodiments of the invention are described in the following specific examples which are not to be construed as limiting.

EXAMPLE 1

Preparation of a Stable 5-Aminolevulinic Acid Solution

The components used for preparing a 5-ALA solution and their relative proportions, are given in Table 1.

TABLE 1

| Ingredient | Quantity Added (% by weight) | Final Quantity (% by weight) |
|---|---|---|
| 5-Aminolevulinic acid hydrochloride | 20.00% | 15.00% |
| Glycolic Acid | 1.0% | 2.0% |
| Lactic Acid | 1.0% | 5.0% |
| Sodium Hyaluronate | 0.5% | 1.0% |
| Sodium Lauryl Sulfate | 0.5% | 0.5% |
| EDTA | 0.5% | 0.5% |
| Glycerin | 3.00% | 3.00% |
| Cremophor A 25 | 1.00% | 1.00% |
| Lidocaine (dissolved in Buffer) | 1.0% | 2.0% |
| Brij-35 (polyoxyethylene) | 0.5% | 1.0% |
| Water (ultra pure) | 69.0% | 49.0% |
| Sorbitol, 70% | 0.5% | 0.5% |
| Isopropyl Alcohol (70%) | 1.0% | 1.0% |
| Polyviny Alcohol | 0.5% | 0.5% |
| Buffer pH 7.1 | 20.00% | 20.00% |

In making the composition, the steps were carried out while excluding light and atmospheric oxygen. The 5-ALA powder was added to 100 mL beaker. The beaker was mounted with the clamp on the magnetic stirrer (High Speed). The 5-ALA was dissolved in water (40 ml) with continuous stirring. To this, the appropriate amounts of ingredients mentioned above were added in the order listed, i.e. components of the carrier. The mixture was stirred continuously at high speed until a clear viscous solution of 15% 5-ALA was obtained. The solution is stable for number of hours. The solution was cooled immediately in an ice bath at −5° C. To optimize shelf life of the solution, the solution is stored at a temperature of 0° C. or less.

The analytical data for the 5-ALA solution described above are set out in Table 2.

TABLE 2

| | |
|---|---|
| Aqueous phase | 20 mM phosphate buffer saline pH 7.1 |
| optical properties | Transparent liquid |
| pH at room temperature | 5.3 |
| viscosity (20° C.) | 1.1 mPas |

EXAMPLE 2

Effect of 5-ALA on Cell Viability

Figure 2:
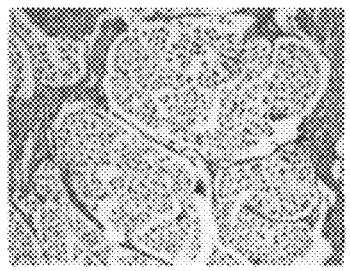
FIG. 2 illustrates significant apoptosis in treated cells (B) in comparison to control (A)
Figure 2:
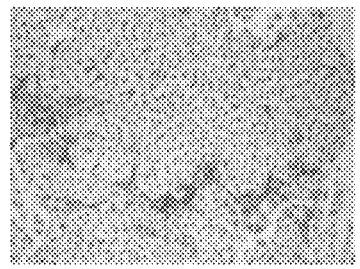

Human glioblastoma U87MG cell line was purchased from the American Type Culture
Collection (Manassas, Va., USA). Cells were grown at 37° C. in 75-cm2 flasks containing 10 ml of 1× RPMI 1640 supplemented with 10% fetal bovine serum (FBS) and 1% penicillin and streptomycin (GIBCO-BRL) in a fully-humidified incubator containing 5% CO2 and 95% air. Following trypsinization using a trypsin/EDTA solution, cells were serially passaged to achieve about 80% confluency. Then, cells were incubated in a low serum condition (1% FBS) for 24 h prior to any treatment and maintained in this low serum condition during all treatments. Cells were treated with a 1 mM 5-ALA composition as described in Example 1, for 30 minutes followed by PDT with a blue light (400-450 nm) at a dose of 23J/cm2 at 37° C. Control cells were not treated with 5-ALA but exposed to blue light.
Trypan Blue Dye Test for Cell Viability
Following all treatments the viability of attached and detached cell populations was estimated by trypan blue dye exclusion test. Trypan blue dye could not penetrate the intact plasma membrane of viable (white) cells but crossed the derelict plasma membrane of dead (blue) cells.
Results
Decrease in Cell Viability After 5-ALA-PDT
Dose-dependently, 5-ALA-PDT decreased cell viability in U87MG cells when compared with control cells. 5-ALA-PDT induced morphological changes in dead cells. Following 5-ALA-PDT, Wright staining showed morphological features of apoptosis in U87MG cells. 5-ALA-PDT induced morphological features such as reduction in cell-volume, chromatin condensation, and/or presence of cell membrane blebbing in U87MG cells indicating occurrence of apoptotic cell death, Compared with control cells, treatment with 1 mM 5-ALA-PDT caused 43% (p<0.0001) apoptosis (see FIG. 2).
Induction of DNA
Induction of DNA fragmentation as a biochemical feature of apoptosis (violet color cell) was examined by ApopTag assay. Control cells showed nochanges in the cell density, confirming almost absence of apoptosis. After 5-ALA-PDT, many cells were apoptotic as indicated by violet staining and also characteristic morphological changes such as cell shrinkage, pyknotic nuclei, cell blebbing, and formation of apoptotic bodies. Compared with control cells, treatment with 1 mM 5-ALA-PDT caused 47% (p<0.0001) apoptosis (see FIG. 3a/b).

Figure 3:
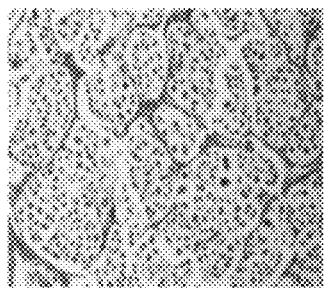
FIG. 3 illustrates significant apoptosis in treated cells (B) in comparison to control (A), and an increase in Bax:Bcl-2 ratio (C) in treated cells.
Figure 3:
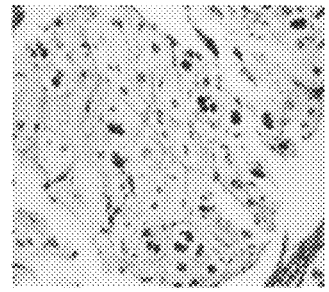
Figure 3:
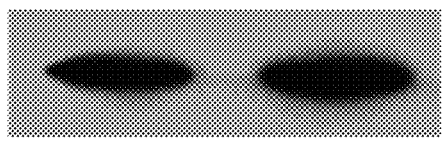

The increase in Bax:Bcl-2 ratio after 5-ALA-PDT indicated a commitment of U87MG cells to apoptosis (see FIG. 3c).

EXAMPLE 3

Treatment of Acne Vulgaris Using 5-ALA Composition

Photodynamic therapy with topical ALA composition as described in Example 1 was tested for the treatment of acne vulgaris, in an open-label prospective human study. 22 subjects with acne on their back were treated at 4 different sites with one of the following at each site: ALA plus red light (ALA-PDT), ALA alone, light alone, and untreated control. Half of the subjects were treated once; half were treated 4 times. 20% topical ALA of Example 1 was applied with 3 hr occlusion, and 150 J/cm$^2$ broad band light (550-700 mm) was applied to the treated site. Sebum excretion rate and autofluorescence from follicular bacteria were measured before, and at 2, 3, 10, and 20 weeks after treatment. Histologic changes and PpIX synthesis in pilosebaceous units were observed from skin biopsies.

ALA-PDT caused a transient acne-like folliculitis. Sebum excretion was eliminated for several weeks, and decreased for 20 weeks after PDT; multiple treatments caused greater suppression of sebum. Bacterial porphyrin fluorescence was also suppressed by PDT. On histology, sebaceous glands showed acute damage and were smaller 20 weeks after PDT. There was clinical and statistically significant clearance of inflammatory acne by ALA-PDT, for at least 20 weeks after multiple ALA-PDT treatments and 10 weeks after a single treatment. Transient hyperpigmentation, superficial exfoliation and crusting were observed, which cleared without scarring. The present methods of the invention provide topical ALA-PDT as an effective treatment of acne vulgaris. ALA-PDT causes phototoxicity to sebaceous follicles, prolonged suppression of sebaceous gland function, and apparent decrease in follicular bacteria after PDT.
Material and Methods
Subject Selection
Twenty-two subjects of both sexes with mild to moderate acne vulgaris (grade 1-4) (Burke et al., 1984) on their faces were enrolled. People were excluded if they had used any topical acne treatment, systemic antibiotics in the previous 2 weeks, or systemic retinoids in the past 1 year. People were also excluded using medication that could exacerbate or alleviate acne, planning to have excessive sunlight exposure, with a history of keloid or photosensitivity disorder, with Fitzpatrick's skin phototype V-VI, and pregnant or lactating women.
Study Design
Subjects were randomly divided into single treatment group or multiple treatment group. At baseline, clinical evaluations, natural bacterial porphyrin fluorescence photography, and sebum excretion rate (SER) evaluation were performed. Prior to treatment, the skin was cleaned with 70% isopropyl alcohol. Then, 20% topical ALA in a novel acidic solution at pH 5 (as described in Example 1) was applied for 10-15 minutes under occlusion with plastic film (Saran wrap), and 150 J/cm$^2$ blue light (400-550 nm) was applied to the ALA-PDT treated site. In the multiple treatment group, subjects were treated once every 15 days (twice a month). In this group, if severe exfoliation, erosions or purpura occurred, treatment was postponed to the following week. In both groups, subjects returned one week after treatments for clinical evaluations and at weeks 2, 3, 10 and 20 for clinical, fluorescence, and SER evaluations.
Clinical Evaluations
Each subject's acne was visually assessed using an inflammatory acne score modified from that previously described (Burke et al., 1994). The modification used in this study accounted for both number and size of acne lesions. The numbers of comedo, inflammatory comedo, papules, pustules, nodules and cysts in each test area were recorded. Each type of lesion was given a severity index as follows: 1 for comedo (<1 mm), 2 for inflammatory comedo, 3 for papule (1 mm-5 mm), 4 for pustule, 5 for nodule (>5 mm), and 6 for inflammatory cyst.

Clinical improvement was globally assessed by 3 dermatologists unaware of the status of treatment, who blindly graded changes in acne from fixed-magnification clinical photographs, after being shown a standardized series of training slides not used in the data evaluation. The grading scale was defined as −3 for >50% exacerbation, −2 for 25+-50% exacerbation, −1 for $1^+$-25% exacerbation, 0 if unchanged, 1 for $1^+$-25% improvement, 2 for $25^+$-50% improvement, 3 for $50^+$-75% improvement, 4 for $75^{30}$-99% improvement, and 5 for 100% improvement, as compared to the baseline.

Photography

Photographs were taken before and after treatment using a visio camera or high resolution Sony Camera. Photographs were taken at the base line and immediately after the treatment and at 3, 5, 7, 15 and 30 days following treatment.

Sebum Excretion Rate (SER) Measurement

Sebum-absorbent tape (Sebutapes) is a non-invasive, easy and reproducible method to evaluate human sebum output. The subject's skin was shaved, then cleansed for 15 seconds with a cotton gauze soaked in 70% ethanol. When the skin was completely dry, a strip of Sebutape was adhered to each test site for an hour. After removal from the skin, the white tape was placed on a black card for image analysis. Small transparent spots due to sebum excretion from follicles were visualized as a black spot on the white background. A CCD camera and digital frame grabber were used to capture images of the sebutape, then examined using a computer-assisted image analysis (IP-LAB) system. The percentage of sebutape area covered by sebum spots (black) was calculated. Sebutape assays of SER were done this way, at weeks, 0, 2, 3, 10, and 20 in all sites.

Adverse Effects

Adverse effects were scored by clinical evaluation of erythema, edema, loss of epidermis, hyperpigmentation, hemorrhage, vesiculation, and exfoliation on a visual-analogue scale from 0 to 3 (0=absent, 1=mild, 2=moderate, 3=severe) for each finding. Subjective sensation of pain, burning, and itching was generally maximum about 10 minutes into light exposure, and was ranked at that time and the end of treatment by subjects on a scale from 0 to 3 similar to above.

Results

Figure 4:
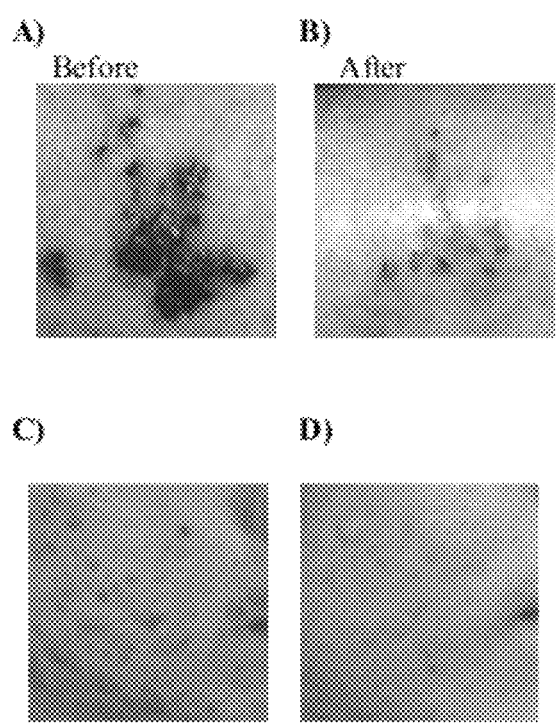
FIG. 4 illustrates skin conditions before (A/C) and after (B/D) treatment with the present ALA composition.
Figure 5:
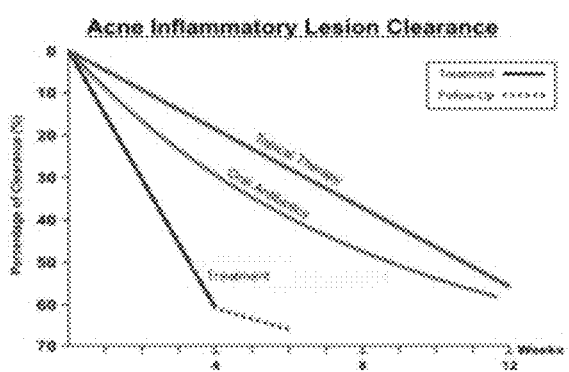
FIG. 5 graphically compares the acne lesion clearance using an ALA composition in accordance with the invention, an anti-microbial treatment and a topical treatment.

There was a rapid response rate to the treatment, which resulted in a decrease in the number of acne lesions (see FIG. 4), as well as improvement in severity scores following the eight bi-weekly 10-minute treatment sessions. The amelioration of acne was comparable to the effects of oral antibiotics; however, the therapeutic effect occurred as early as four weeks after treatment (as compared to eight to twelve weeks using antibiotics or a topical treatment such as Benzoyl Peroxide or Salicylic acid lotion) (see FIG. 5) and without the side effects associated with topical or parenteral anti-acne medications, such as burning, peeling, scaling of the skin along with severe dryness and redness.

These results demonstrate that the present ALA composition is an effective treatment for intractable acne vulgaris. A single session of 20 J/cm2 irradiation prevented the development of new lesions during a follow-up period of 8 weeks without causing adverse effects. All patients felt very little discomfort during the exposure to the light or laser irradiation and tolerated the therapy well. The formulation was well tolerated by all the subjects.

EXAMPLE 4

Preparation of a Peroxide-Containing 5-Aminolevulinic Acid Solution

The components used for preparing a peroxide-containing 5-ALA solution and their relative proportions, are given in Table 2. The solution was prepared as described in Example 1.

TABLE 2

| Ingredient | Formulation-1 (% by weight) | Formulation-2 (% by weight) |
| --- | --- | --- |
| 5-Aminolevulinic acid hydrochloride | 20.00% | 15.00% |
| Glycolic Acid | 3.0% | 2.0% |
| Lactic Acid | 3.0% | 5.0% |
| Sodium Hyaluronate | 0.5% | 1.0% |
| Sodium Lauryl Sulfate | 0.5% | 0.5% |
| EDTA | 0.5% | 0.5% |
| Glycerin | 3.00% | 3.00% |
| Cremophor A 25 | 1.00% | 1.00% |
| Lidocaine (dissolved in Buffer) | 1.0% | 2.0% |
| Brij-35 (polyoxyethylene) | 0.5% | 1.0% |
| Water (ultra pure) | 61.0% | 45.0% |
| Sorbitol, 70% | 0.5% | 0.5% |
| Isopropyl Alcohol (70%) | 2.0% | 2.0% |
| Hydrogen Peroxide | 3.0% | 3.0% |
| Polyviny Alcohol | 0.5% | 0.5% |
| Buffer pH 7.1 | 20.00% | 20.00% |

Treatment using the peroxide-containing 5-ALA composition, and the protocol as essentially described in Example 3, resulted in reduced treatment times in the treatment of skin conditions such as acne and actinic keratosis. Specifically, the peroxide-containing 5-ALA composition was applied to a target site (site of acne and a site of actinic keratosis), and 10 minutes following application of the composition, the treated area was irradiated with the light at a wavelength between 410 and 650 nm for 10 minutes.

The peroxide-containing 5-ALA composition was active at the treated sites, which exhibited noticeable reduction in lesion size and number as compared to traditional topical therapies. Two weeks following the first treatment there was approximately 40%+ improvement in lesion count, and following a second treatment (similar to the first treatment as set out above,), at 6 weeks from the first treatment, an approximately 77% improvement in lesion count was observed.

Accordingly, the peroxide-containing 5-ALA composition enhances the effect of the 5-ALA composition.

What is claimed is:

1. A composition comprising:
   (a) an active ingredient selected from the group of 5-aminolevulinic acid or a pharmaceutically acceptable salt or derivative thereof in an amount of 10-30% by wt; and
   (b) a micelle-forming aqueous carrier in an amount of 40-60% by wt
   comprising sodium lauryl sulfate, EDTA, cremaphor A 25, glycerin, polyoxyethylene, isopropyl alcohol, polyvinyl alcohol and sorbitol in an amount ranging from 0.1-10% by wt; an anesthetic in an amount of 0.1-10% by wt and selected from the group consisting of Lidocaine, bupivacaine, prilocaine, benzocaine, tetracaine, lanacaine, mepivacaine and combinations thereof; a non-fatty acid selected from the group consisting of hyaluronic acid in an amount of 0.1-2% by wt, lactic acid 1-5% by wt and glycolic acid 1-3% by wt; and
   the balance of the carrier being water; and
   (c) an acidic phase which imparts on the composition a pH of less than 7.

2. The composition according to claim 1, wherein the carrier further comprises an absorption enhancer is selected from the group consisting of sodium lauryl sulfate, DMSO, bile salts, compound selected from the group comprising lecithin, hyaluronic acid, octylphenoxypolyethoxyethanol, glycolic acid, lactic acid, chamomile extract, cucumber extract, oleic acid, linoleic acid, linolenic acid, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate, deoxycholate, benzyl alcohol, carbomer 940, cholesterol, hydrogenated lecithin, polysorbate 80, propylene glycol, trolamine, vitamin E acetate, lidocaine, benzyl alcohol, carbomer 940, cholesterol, hydrogenated lecithin, polysorbate 80, propylene glycol, trolamine, vitamin E acetate, and combinations thereof.

3. The composition, of claim 1 wherein the active ingredient is present in a proportion of from 10% to 25% by weight based on the total weight of the composition.

4. The composition of claim 3, wherein the composition is in the form of a gel and, based on the total weight of the composition, comprises from 10% to 15% of active ingredient, from 40 to 55% of carrier, with the remainder being water.

5. The composition of claim 3, wherein the composition is in the form of a lotion or gel, and based on the total weight of the composition, comprises from 10 to 15% of active ingredient, and from 40 to 60% of carrier with the balance of the carrier being water.

6. The composition of claim 1, wherein the composition additionally comprises cosmetic or pharmaceutical adjuvants.

7. The composition according to claim 1, wherein the carrier comprises 0.1-2% HA, 0.1-2% Polyvinyl Alcohol, 1-3% glycolic acid, 1-5% lactic acid and 0.1-10% anaesthetic, based on the total weight of the composition.

8. The composition of claim 7, wherein the anaesthetic is selected from the group consisting of Lidocaine, bupivacaine, prilocaine, benzocaine, tetracaine, lanacaine, mepivacaine and combination thereof.

9. The composition of claim 1, additionally comprising an oxygen radical generating compound or oxygen-containing compound.

10. The composition as defined in claim 9, comprising a compound selected from the group consisting of hydrogen peroxide, benzoyl peroxide and a perfluorocarbon.

11. A kit comprising a topically applicable composition as defined in claim 1 further comprising (a) an essentially light-impermeable sheet-like material, (b) means for attaching the sheet-like material to a site of application, and (c) means for applying the composition to a site of application.

12. The composition of claim 1, wherein the carrier comprises 0.5% by wt sodium lauryl sulfate, 0.5% by wt EDTA, 1% by wt cremaphor A 25, 3% by wt glycerin, 0.5-1% by wt polyoxyethylene, 1-2% by wt isopropyl alcohol, 0.5% by wt polyvinyl alcohol and 0.5% by wt sorbitol.

13. The composition of claim 1, wherein the carrier comprises 1-2% by wt of the anaesthetic.

14. The composition of claim 13, wherein the anaesthetic is lidocaine.

15. The composition of claim 1, wherein the composition additionally comprises cosmetic or pharmaceutical adjuvants.

16. The composition as defined in claim 1, further comprising a compound selected from the group consisting of hydrogen peroxide, benzoyl peroxide and a perfluorocarbon.

* * * * *